(12) United States Patent
Laroche et al.

(10) Patent No.: US 9,421,492 B2
(45) Date of Patent: Aug. 23, 2016

(54) AMINOPYRIDINE DERIVATIVES FOR REMOVAL OF HYDROGEN SULFIDE FROM A GAS MIXTURE

(75) Inventors: Christophe R. Laroche, Lake Jackson, TX (US); Gerardo Padilla, Lake Jackson, TX (US)

(73) Assignee: Dow Global Technologies LLC, Midland, MI (US)

(*) Notice: Subject to any disclaimer, the term of this patent is extended or adjusted under 35 U.S.C. 154(b) by 409 days.

(21) Appl. No.: 14/234,506

(22) PCT Filed: Jul. 17, 2012

(86) PCT No.: PCT/US2012/047016
§ 371 (c)(1),
(2), (4) Date: Mar. 18, 2014

(87) PCT Pub. No.: WO2013/016063
PCT Pub. Date: Jan. 31, 2013

(65) Prior Publication Data
US 2014/0234191 A1    Aug. 21, 2014

Related U.S. Application Data

(60) Provisional application No. 61/512,558, filed on Jul. 28, 2011.

(51) Int. Cl.
*B01D 53/14* (2006.01)
*C07D 213/74* (2006.01)
*B01D 53/52* (2006.01)

(52) U.S. Cl.
CPC ........ *B01D 53/1468* (2013.01); *B01D 53/1493* (2013.01); *B01D 53/52* (2013.01); *C07D 213/74* (2013.01); *B01D 2252/103* (2013.01); *B01D 2252/20415* (2013.01); *B01D 2252/20426* (2013.01); *B01D 2252/20431* (2013.01); *B01D 2252/20447* (2013.01); *B01D 2252/20457* (2013.01); *B01D 2252/20484* (2013.01)

(58) Field of Classification Search
None
See application file for complete search history.

(56) References Cited

U.S. PATENT DOCUMENTS

| 4,471,138 A | 9/1984 | Stogryn |
| 4,618,481 A | 10/1986 | Heinzelmann et al. |
| 4,959,086 A | 9/1990 | Van Baar et al. |
| 7,427,383 B2 | 9/2008 | Cisneros |

FOREIGN PATENT DOCUMENTS

EP    0322924    7/1989

*Primary Examiner* — Jennifer A Smith
*Assistant Examiner* — Anita Nassiri Motlagh

(57) ABSTRACT

The present invention relates to a novel class of aminopyridine derivatives with the general formula: wherein $R_1$; $R_2$, $R_3$, and $R_4$ are each independently hydrogen, an alkyl group, —(O—CH$_2$—CH2)$_n$-OH wherein n is an integer from 0 to 8, —CH$_2$—(O—CH$_2$—CH$_2$)n-OH wherein n is an integer from 0 to 8, an hydroxyalkyl group, an aminoalkyl group where the nitrogen can be part of a 5 or 6 ring membered cycle, an alkylene group containing quaternary ammonium, a carboxylic acid and/or a salt thereof, or a sulphonic acid and/or a salt thereof, preferably $R_1$; $R_2$, $R_3$, and $R_4$ are each hydrogen. The compounds are useful for removal of hydrogen sulfide and other impurities from fluid streams containing hydrogen sulfide, including selective removal from such streams which also contain carbon dioxide. Examples of the fluid stream include a gas stream, for example natural gas, synthesis gas, tail gas, refinery gas, or from liquid streams such as liquid or liquefied hydrocarbons, for example Liquefied Petroleum Gas or Natural Gas Liquids.

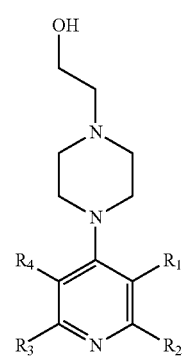

6 Claims, No Drawings

AMINOPYRIDINE DERIVATIVES FOR REMOVAL OF HYDROGEN SULFIDE FROM A GAS MIXTURE

FIELD OF THE INVENTION

The present invention relates to a class of aminopyridine derivatives and their use for removing hydrogen sulfide from fluid streams, normally gaseous streams, containing hydrogen sulfide, including selective removal from such streams which also contain carbon dioxide.

BACKGROUND OF THE INVENTION

Fluid streams derived from natural gas reservoirs, petroleum or coal, often contain a significant amount of acid gases, for example carbon dioxide ($CO_2$), hydrogen sulfide ($H_2S$), sulfur dioxide ($SO_2$), carbon disulfide ($CS_2$), hydrogen cyanide (HCN), carbonyl sulfide (COS), or mercaptans as impurities. Said fluid streams may be gas, liquid, or mixtures thereof, for example gases such as natural gas, refinery gas, hydrocarbon gasses from shale pyrolysis, synthesis gas, and the like or liquids such as liquefied petroleum gas (LPG) and natural gas liquids (NGL).

Various compositions and processes for removal of acid gasses are known and described in the literature. It is well-known to treat such fluid streams with amine solutions to remove these acidic gases. The amine usually contacts the acidic gases and the liquids as an aqueous solution containing the amine in an absorber tower with the aqueous amine solution contacting the acidic fluid counter currently.

The most widely used amines are monoethanolamine (MEA) and diethanolamine (DEA) which are most commonly made by reacting ethylene oxide and ammonia. Both amines are irritants to the skin. Ethylene oxide is an irritant to the eyes and skin, and is a suspected human carcinogen; it is also highly flammable, a fire danger and has a high explosive risk. Further, anhydrous ammonia may be fatal in concentrated form, poses a moderate fire risk, and may reach explosive limits in air.

The removal of sulfur compounds from these fluid streams is of particular importance for various reasons. For instance, the level of sulfur compounds in natural gas has to be reduced by suitable processing measures immediately at the source of a natural gas, since the natural gas will customarily also contain a certain fraction of entrained water as well as the above-recited sulfur compounds. In aqueous solution, however, these sulfur compounds are present as acids and have a corrosive effect. To transport natural gas in a pipeline, therefore, predetermined limits must be complied with for the sulfur-containing impurities. In addition, numerous sulfur compounds are malodorous and, with $H_2S$ a prime example, extremely toxic even at low concentrations.

Similarly, the $CO_2$ content of hydrocarbonaceous gases, such as natural gas, customarily has to be significantly reduced, since high concentrations of $CO_2$ reduce the calorific value of the gas and may likewise cause corrosion to pipework and fittings.

However, it is often desirable to treat acid gas mixtures containing both $CO_2$ and $H_2S$ so as to remove the $H_2S$ selectively from the mixture, thereby minimizing removal of the $CO_2$. Selective removal of $H_2S$ results in a relatively high $H_2S/CO_2$ ratio in the separated acid gas which simplifies the conversion of $H_2S$ to elemental sulfur.

The European patent application EP0322924 discloses, for example, that tertiary alkanolamines, especially methyldiethylanolamine (MDEA), are particularly suitable for a selective removal of $H_2S$ from gas mixtures containing $H_2S$ and $CO_2$. However, in mixtures having a high concentration of $CO_2$, it has been found to be disadvantageous that the effectiveness of the solution for removing $H_2S$ is much reduced by an accelerated absorption of $CO_2$.

It is also known to use a liquid absorbent containing a severely hindered amino compound for the selective removal of hydrogen sulfide from normally gaseous mixtures. See, for example, U.S. Pat. No. 4,471,138, the teachings of which are hereby incorporated by reference. However, this method cannot provide for low levels of $H_2S$ levels, for example lower than 10 parts per million (ppm).

U.S. Pat. No. 4,618,481, which is incorporated by reference herein in its entirety, discloses the absorption of hydrogen sulfide by the use of an alkaline absorbent composition comprising a severely hindered amine and an amine salt to produce a treated gas having less than 10 ppm hydrogen sulfide. However, this method shows a significant decrease in capacity.

U.S. Pat. No. 7,427,383 discloses contacting gaseous streams containing $H_2S$ with an aqueous silicon-containing composition; however, this method is ineffectual in reducing $H_2S$ content unless high shear conditions are employed.

U.S. Pat. No. 4,959,086, which is incorporated herein in its entirety, discloses a process for removing $H_2S$ from a gas mixture by contacting the gas mixture with a liquid absorbent composition comprising an aminopyridine, such as 4-dimethylaminopyridine. However, said compounds demonstrate limited solubility in water and generally require a suitable solvent such as lower alkane diols, polyols, alkyl ethers, esters, sulfolans, and the like for practical application.

As such, there is a need for a class of compounds, and method to use said compounds, to remove hydrogen sulfide selectively in the presence of carbon dioxide from fluid streams, which does not require specialized equipment, e.g., high shear; is effective over a broad range of carbon dioxide concentrations, and demonstrates an improved solubility in water.

SUMMARY OF THE INVENTION

In one embodiment, the present invention is class of compounds for use in removing hydrogen sulfide selectively in the presence of carbon dioxide from fluid streams, said compound is a 1-hydroxyethyl-4-pyridinlypiperazine of the general formula:

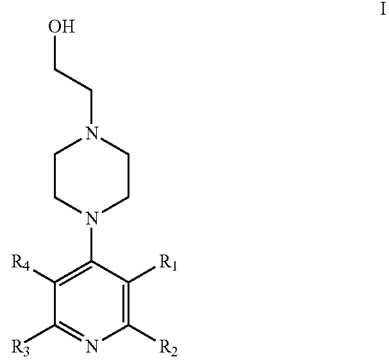

I wherein $R_1$, $R_2$, $R_3$, and $R_4$ are each independently hydrogen, an alkyl group, $-(O-CH_2-CH_2)_n-OH$ wherein n is an integer from 0 to 8, $-CH_2-(O-CH_2-CH_2)_n-OH$ wherein n is an integer from 0 to 8, an hydroxyalkyl group, an aminoalkyl group where the nitrogen can be part of a 5 or 6 ring membered cycle, an alkylene group containing quaternary ammonium, a carboxylic acid and/or a salt thereof, or a sulphonic acid and/or a salt thereof, preferably $R_1$, $R_2$, $R_3$, and $R_4$ are all hydrogen, preferably the above mentioned 1-hydroxyethyl-4-pyridinlypiperazine compound is comprised in an aqueous absorbent solution wherein in an amount of from 0.1 to 60 percent by weight of the aqueous absorbent solution.

A preferred embodiment of the present invention is a process for removing hydrogen sulfide from a fluid stream including hydrogen sulfide, and optionally further comprising carbon dioxide, comprising the step of contacting the fluid stream with an aqueous absorbent solution comprising the 1-hydroxyethyl-4-pyridinlypiperazine compound disclosed herein above, preferably wherein $R_1$, $R_2$, $R_3$, and $R_4$ are all hydrogen, preferably the aqueous absorbent composition comprises the 1-hydroxyethyl-4-pyridinlypiperazine compound in an amount from 0.1 to 60 weight percent based on the weight of the aqueous absorbent composition.

In a preferred embodiment of the above disclosed process, the aqueous absorbent composition further comprising from 0.1 to 95 weight percent of one or more amino compound wherein weight percent is based on the weight of the aqueous absorbent composition, preferably the one or more amino compound is monoethanolamine, diethanolamine, methylethanolamine, monoisopropanolamine, diisopropanolamine, 2-hydroxyethylpiperazine, piperazine, 1-methylpiperazine, 2-methylpiperazine, 2-(2-aminoethoxy) ethanol, tris(2-hydroxyethyl)amine; tris(2-hydroxypropyl)amine; tributanolamine; bis(2-hydroxyethyl)methylamine; 2-diethylaminoethanol; 2-dimethylaminoethanol; 3-dimethylamino-1-propanol; 3-diethylamino-1-propanol; 2-diisopropylaminoethanol; N,N-bis(2-hydroxypropyl)methylamine; N,N'-bis(2-hydroxyethyl)piperazine, 2-(2-aminoethoxy) ethanol, 2-amino-2-methyl-1-propanol, 1-amino-2-methylpropan-2-ol, 2-(2-tertiarybutylamino) propoxyethanol, 2-(2-tertiarybutylamino)ethoxyethanol, 2-(2-isopropylamino)propoxyethanol, tertiaryamylaminoethoxyethanol, or (1-methyl-2-ethylpropylamino)ethoxyethanol.

In a preferred embodiment of the process disclosed herein above, the aqueous absorbent composition consists essentially of water and the 1-hydroxyethyl-4-pyridinlypiperazine compound.

Preferably, for any of the processes disclosed herein above, the fluid stream is natural gas, synthesis gas form heavy oil, synthesis gas, tail gas, refinery gas, or synthesis gas from liquid or liquefied hydrocarbons.

DETAILED DESCRIPTION OF THE INVENTION

The present invention comprises a class of 1-hydroxyethyl-4-pyridinlypiperazine compounds which, when comprised in an absorbent aqueous composition, are effective in removing hydrogen sulfide, preferably selectively removing hydrogen sulfide ($H_2S$) in the presence of one or more other acid gas impurities, for example carbon dioxide ($CO_2$), sulfur dioxide ($SO_2$), carbon disulfide ($CS_2$), hydrogen cyanide (HCN), carbonyl sulfide (COS), ammonia ($NH_3$), or mercaptans, from fluid streams. Moreover, these 1-hydroxyethyl-4-pyridinlypiperazine compounds have shown improved solubility in water as well as high selectivity for hydrogen sulfide over carbon dioxide when carbon dioxide is also present in the fluid stream.

The specific class of 1-hydroxyethyl-4-pyridinlypiperazine compounds is described by the following formula:

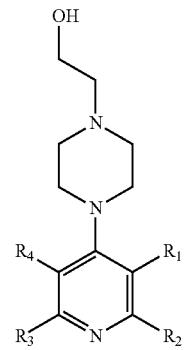

I wherein $R_1$, $R_2$, $R_3$, and $R_4$ are each independently hydrogen, an alkyl group, —(O—CH$_2$—CH$_2$)$_n$—OH wherein n is an integer from 0 to 8, —CH$_2$—(O—CH$_2$—CH$_2$)$_n$—OH wherein n is an integer from 0 to 8, an hydroxyalkyl group, an aminoalkyl group where the nitrogen can be part of a 5 or 6 ring membered cycle, an alkylene group containing quaternary ammonium, a carboxylic acid and/or a salt thereof, or a sulphonic acid and/or a salt thereof, preferably $R_1$, $R_2$, $R_3$, and $R_4$ are each hydrogen. In the 1-hydroxyethyl-4-pyridinlypiperazine compounds of the invention, the alkyl and alkoxy groups can contain from 1 to about 10 carbon atoms, preferably from 1 to about 4 carbon atoms.

The 1-hydroxyethyl-4-pyridinlypiperazine compound is provided in an aqueous absorbent composition comprising water and the 1-hydroxyethyl-4-pyridinlypiperazine compound. The amount of 1-hydroxyethyl-4-pyridinlypiperazine compound in solution may range from equal to or greater than 0.1 weight percent, preferably equal to or greater than 1 weight percent, more preferably equal to or greater than 5 weight percent based the total weight of the aqueous absorbent composition. The amount of 1-hydroxyethyl-4-pyridinlypiperazine compound in solution may range from equal to or less than 60 weight percent, preferably equal to or less than 50 weight percent, more preferably equal to or less than 25 weight percent based the total weight of the aqueous absorbent composition.

The aqueous absorbent composition of the present invention may optionally contain one or more additional amino compound. Preferably, the additional amino compound is an alkanolamine (aminoalcohol) such as tris(2-hydroxyethyl)amine (triethanolamine, TEA); tris(2-hydroxypropyl)amine (triisopropanol); tributanolamine; bis(2-hydroxyethyl)methylamine (methyldiethanolamine, MDEA); 2-diethylaminoethanol (diethylethanolamine, DEEA); 2-dimethylaminoethanol (dimethylethanolamine, DMEA); 3-dimethylamino-1-propanol; 3-diethylamino-1-propanol; 2-diisopropylaminoethanol (DIEA); N,N-bis(2-hydroxypropyl)methylamine (methyldiisopropanolamine, MDIPA) or N,N'-bis(2-hydroxyethyl)piperazine (dihydroxyethylpiperazine, DiHEP).

Preferred additional amino compounds comprise one or more tertiary amino group.

Preferably the additional amino compound has one or more sterically hindered amino group. An aqueous absorption composition comprising a 1-hydroxyethyl-4-pyridinlypiperazine compound and an amine having one or more sterically hindered amino group is particularly suitable for the selective removal of $H_2S$.

As used herein, "sterically hindered amino group" includes:

(i) a primary amino group which is bound to a tertiary carbon atom,
(ii) an amino group which is bound to a secondary or tertiary carbon atom, and/or
(iii) an amino group, wherein a tertiary or quaternary carbon atom is arranged in the β position to the amino group.

Examples of an amine having a sterically hindered amino group suitable for use in the present invention are 2-amino-2-methyl-1-propanol (AMP), 1-amino-2-methylpropan-2-ol, 2-(2-tertiarybutylamino)propoxyethanol, 2-(2-tertiarybutylamino)ethoxyethanol, 2-(2-isopropylamino)propoxyethanol, tertiaryamylaminoethoxyethanol, and (1-methyl-2-ethylpropylamino)ethoxyethanol.

If present, the amount of optional amino compound in solution may range from equal to or greater than 0.1 weight percent, preferably equal to or greater than 5 weight percent, more preferably equal to or greater than 20 weight percent based the total weight of the aqueous absorbent composition. If present, the amount of optional amino compound in solution may range from equal to or less than 95 weight percent, preferably equal to or less than 50 weight percent, more preferably equal to or less than 25 weight percent based the total weight of the aqueous absorbent composition. In a preferred embodiment, the aqueous absorbent composition contains 5 to 10 weight percent 1-hydroxyethyl-4-pyridinlypiperazine compound and 20 to 40 weight percent MDEA, weight percent based on the total weight of the aqueous absorbent composition.

The 1-hydroxyethyl-4-pyridinlypiperazine compound solution may be provided alone or in combination with one or more other compounds used in fluid treatment following well known practices. Illustrative compounds which may optionally be provided include, but are not limited to, one or more of the following: antifoaming agents; physical solvents including glycols and the mono- and di-ethers or esters thereof, aliphatic acid amides, N-alkylated pyrrolidones, sulfones, sulfoxides and the like; antioxidants; corrosion inhibitors; film formers; chelating agents such as metals; pH adjusters such as alkali compounds; and the like. The amount of these optional components is not critical but may be provided in an effective amount following known practices.

In a preferred embodiment, the aqueous absorbent composition of the present invention does not contain a physical solvent, in other words, the aqueous absorbent composition comprises one or more 1-hydroxyethyl-4-pyridinlypiperazine compound, optionally one or more additional amino compound, optionally one or more other compounds used in fluid treatment listed above, and water, but no physical solvent (e.g., glycols and the mono- and di-ethers or esters thereof, aliphatic acid amides, N-alkylated pyrrolidones, sulfones, sulfoxides and the like).

The invention set forth herein has great application in the petrochemical and energy industries. For example, the present invention can be used for the treatment of fluid streams, gas, liquid, or mixtures, in an oil refinery, the treatment of sour gas, the treatment of coal seam gas, the treatment of hazardous stack emissions, the treatment of land field gasses, and a new series of devices dealing with hazardous emissions for human safety.

The fluid streams to be treated by the process of the present invention contain an acid gas mixture which includes $H_2S$, and may optionally include other gases such as $CO_2$, $N_2$, $CH_4$, $H_2$, CO, $H_2O$, COS, HCN, $NH_3$, mercaptans, and the like. Often such gas mixtures are found in combustion gases, refinery gases, town gas, natural gas, syn gas, tail gas, water gas, propane, propylene, heavy hydrocarbon gases, etc. The absorbent composition herein is particularly effective when the fluid stream is a gas, obtained, for example, from shale oil retort gas, coal or gasification of heavy oil with air/steam or oxygen/steam thermal conversion of heavy residual oil to lower molecular weight liquids and gases, or in sulfur plant tail gas clean-up operations.

The process of the present invention is preferably used to selectively remove $H_2S$ from a gas stream comprising $H_2S$ optionally in the presence of one or more other acid gas impurities, for example $CO_2$, $N_2$, $CH_4$, $H_2$, CO, $H_2O$, COS, HCN, $NH_3$, and/or mercaptans. However, the present invention may be used to remove $H_2S$ and one or more of $CO_2$, $N_2$, $CH_4$, $H_2$, CO, $H_2O$, COS, HCN, $NH_3$, and/or mercaptans from a gas stream comprising $H_2S$ and one or more of $CO_2$, $SO_2$, $CS_2$, HCN, COS, and/or mercaptans. Furthermore, the process of the present invention may be used to remove one or more of $CO_2$, $N_2$, $CH_4$, $H_2$, CO, $H_2O$, COS, HCN, $NH_3$, and/or mercaptans from a gas stream not comprising $H_2S$.

The absorption step of this invention generally involves contacting the fluid stream, preferably gaseous stream, with the absorbent composition in any suitable contacting vessel. In such processes, the fluid stream containing $H_2S$ and optionally $CO_2$ and/or other impurities from which the $H_2S$ is to be removed may be brought into intimate contact with the absorbent composition using conventional means, such as a tower or vessel packed with, for example, rings or with sieve plates, or a bubble reactor.

In a typical mode of practicing the invention, the absorption step is conducted by feeding the fluid stream into the lower portion of the absorption tower while fresh aqueous absorbent composition is fed into the upper region of the tower. The fluid stream, freed largely from the $H_2S$, emerges from the upper portion of the tower, and the loaded aqueous absorbent composition, which contains the selectively absorbed $H_2S$, leaves the tower near or at its bottom. Preferably, the inlet temperature of the absorbent composition during the absorption step is in the range of from about 20° C. to about 100° C., and more preferably from 40° C. to about 60° C. Pressures may vary widely; acceptable pressures are between 5 and 2,000 pounds per square inch (psi), preferably 20 to 1,500 psi, and most preferably 25 to 1,000 psi in the absorber. The contacting takes place under conditions such that the $H_2S$ is preferably selectively absorbed by the solution. The absorption conditions and apparatus are designed so as to minimize the residence time of the aqueous absorbent composition in the absorber to reduce $CO_2$ pickup while at the same time maintaining sufficient residence time of the fluid stream with the aqueous absorbent composition to absorb a maximum amount of the $H_2S$ gas. The amount of the aqueous absorbent composition required to be circulated to obtain a given degree of $H_2S$ removal will depend on the chemical structure and basicity of the 1-hydroxyethyl-4-pyridinlypiperazine compound and any additional amino compounds and on the partial pressure of $H_2S$ in the fluid stream. Fluid streams with low partial pressures, such as those encountered in thermal conversion processes, will require more the aqueous absorbent composition under the same absorption conditions than fluid streams with higher partial pressures such as shale oil retort gases.

A typical procedure for the selective $H_2S$ removal phase of the process comprises selectively absorbing $H_2S$ via countercurrent contact of a gaseous mixture containing $H_2S$ and $CO_2$ with the aqueous absorbent composition of the 1-hydroxyethyl-4-pyridinylpiperazine compound and optional additional amino compounds in a column containing a plurality of trays at a low temperature, e.g., below 45° C., and at a gas velocity of at least about 0.3 feet per second (ft/sec, based on "active" or aerated tray surface), depending on the operating pressure of the gas, said tray column having fewer than 20 contacting trays, with, e.g., 4 to 16 trays being typically employed.

After contacting the fluid stream with the aqueous absorbent composition, which becomes saturated or partially saturated with $H_2S$, the solution may be at least partially regenerated so that it may be recycled back to the absorber. As with absorption, the regeneration may take place in a single liquid phase. Regeneration or desorption of the acid gases from the aqueous absorbent composition may be accomplished by conventional means of heating, expansion, stripping with an inert fluid, or combinations thereof, for example pressure reduction of the solution or increase of temperature to a point at which the absorbed $H_2S$ flashes off, or by passing the solution into a vessel of similar construction to that used in the absorption step, at the upper portion of the vessel, and passing an inert gas such as air or nitrogen or preferably steam upwardly through the vessel. The temperature of the solution during the regeneration step should be in the range from about 50° C. to about 170° C., and preferably from about 80° C. to 120° C., and the pressure of the solution on regeneration should range from about 0.5 psi to about 100 psi, preferably 1 psi to about 50 psi. The aqueous absorbent composition, after being cleansed of at least a portion of the $H_2S$ gas, may be recycled back to the absorbing vessel. Makeup absorbent may be added as needed.

In a preferred regeneration technique, the $H_2S$-rich aqueous solution is sent to the regenerator wherein the absorbed components are stripped by the steam which is generated by boiling the solution. Pressure in the flash drum and stripper is usually 1 psi to about 50 psi, preferably 15 psi to about 30 psi, and the temperature is typically in the range from about 50° C. to 170° C., preferably about 80° C. to 120° C. Stripper and flash temperatures will, of course, depend on stripper pressure; thus at about 15 psi to 30 psi stripper pressures, the temperature will be about 80° C. to about 120° C. during desorption. Heating of the solution to be regenerated may very suitably be affected by means of indirect heating with low-pressure steam. It is also possible, however, to use direct injection of steam.

A preferred embodiment of the present invention involves performing the method of the present invention continuously, or as a continuous process. However, the method may be performed batch wise or semi-continuously. Selection of the type of process used should be determined by the conditions, equipment used, type and amount of gaseous stream, and other factors apparent to one of ordinary skill in the art based on the disclosure herein.

EXAMPLES

The following compounds are used in the examples:
"MDEA" is methyldiethanolamine available in 99 percent purity from The Dow Chemical Company;
"DMAP" is 4-dimethylaminopyridine available in 99 percent purity from Aldrich;
"DMAPP" is 2-methyl-4-(dimethylamino)pyridine is prepared according to the procedure described in *Synthetic Communications*, 38(21), 3672-3682; 2008;
"DMAPL" is 2,6-dimethyl-4-(dimethylamino)pyridine is prepared according to the procedure described in *Synthetic Communications*, 38(21), 3672-3682; 2008; and
"HEPP" is 1-hydroxyethyl-4-pyridynyl-pyperazine and is prepared as follows:
a three necked round bottom flak equipped with a reflux condenser is charged with 1-hydroxyethylpiperazine (195.285 g, 1.5 mol), distilled water (200 g), and 4-chloro-pyridium hydrochloride salt (75.005 g, 0.5 mol). The reaction mixture is brought to reflux for 5 hours then cooled down to room temperature. The reaction mixture is extracted using chloroform (5 times, 400 ml). The organic phase is dried with sodium sulfate and the solvent is evaporated under vacuum to give 98.453 g (95 percent yield) of 90 percent pure HEPP. The crude is purified by recrystallization from isopropanol-heptane mixture to give HEPP in a purity of at least 95 percent.

Solubility in unbuffered water is determined for Example 1 and Comparative Examples A to C by dissolving incremental amounts (0.5 g) of material in 50 g of de-ionized water at 25° C. The experiment is repeated three times and the average solubilities are reported as weight percent (wt %) in Table 1.

TABLE 1

| Comparative Example | Example | Compound | Solubility, wt % |
|---|---|---|---|
| A | | DMAP | 8 |
| B | | DMAPP | 5 |
| C | | DMAPL | 3 |
| | 1 | HEPP | 60 |

The performance of Example 2 and Comparative Example D are evaluated in a bench scale glass absorber-stripper apparatus with the following characteristics:

a) gas feed is 8.8 mole percent $CO_2$, 4 mole percent $H_2S$, and the balance nitrogen, feed rate is about 9.9 l/min at 104° F. and 67 psia, b) liquid feed rate is about 44 cc/min at 118° F., c) absorber and stripper staging: random packing, 25 trays absorber, 20 trays stripper, d) amine additive(s) used: about 25 percent by weight, and e) gas phase analysis is done by gas chromatography.

The results obtained in the performance evaluation of Example 2 and Comparative Example D are provided in Table 2 below.

TABLE 2

| | Comparative Example D | Example 2 |
|---|---|---|
| Solution Flow Rate, ml/min | 43.9 | 43.6 |
| Solution Composition, wt % | | |
| MDEA | 25 | 20 |
| HEEP | | 5 |
| Outlet Gas Analysis, ppm | | |
| $CO_2$ | 50,000 | 56,000 |
| $H_2S$ | 490 | 13 |

The Example 2 performs 30 fold better in removing $H_2S$ out of the gas stream and absorbs 10 percent less $CO_2$ compared to Comparative Example D.

The invention claimed is:

1. A process for removing hydrogen sulfide from a fluid stream including hydrogen sulfide comprising the step of contacting the fluid stream with an aqueous absorbent composition comprising a 1-hydroxyethyl-4-pyridnlypiperazine compound of the general formula:

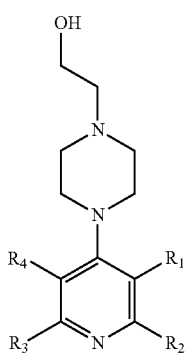

wherein $R_1$, $R_2$, $R_3$, and $R_4$ are each independently hydrogen, an alkyl group, —(O—CH$_2$—CH$_2$)$_n$—OH wherein n is an integer from 0 to 8, —CH$_2$—(O—CH$_2$—CH$_2$)$_n$—OH wherein n is an integer from 0 to 8, an hydroxyalkyl group, an aminoalkyl group where the nitrogen can be part of a 5 or 6 ring membered cycle, an alkylene group containing quaternary ammonium, a carboxylic acid and/or a salt thereof, or a sulphonic acid and/or a salt thereof.

2. The process of claim 1 wherein $R_1$, $R_2$, $R_3$, and $R_4$ are all hydrogen.

3. The process of claim 1 wherein the aqueous absorbent composition comprises from 0.1 to 60 weight percent of the 1-hydroxyethyl-4-pyridnlypiperazine compound wherein weight percent is based on the weight of the aqueous absorbent composition.

4. The process of claim 3 further comprising from 0.1 to 95 weight percent of one or more amino compound wherein weight percent is based on the weight of the aqueous absorbent composition.

5. The process of claim 3 wherein the one or more amino compound is monoethanolamine, diethanolamine, methylethanolamine, monoisopropanolamine, diisopropanolamine, 2-hydroxyethylpiperazine, piperazine, 1-methylpiperazine, 2-methylpiperazine, 2-(2-aminoethoxy)ethanol, tris(2-hydroxyethyl)amine; tris(2-hydroxypropyl)amine; tributanolamine; bis(2-hydroxyethyl)methylamine; 2-diethylaminoethanol; 2-dimethylaminoethanol; 3-dimethylamino-1-propanol; 3-diethylamino-1-propanol; 2-diisopropylaminoethanol; N,N-bis(2-hydroxypropyl)methylamine; N,N'-bis(2-hydroxyethyl)piperazine, 2-(2-aminoethoxy)ethanol, 2-amino-2-methyl-1-propanol, 1-amino-2-methylpropan-2-ol, 2-(2-tertiarybutylamino)propoxyethanol, 2-(2-tertiarybutylamino)ethoxyethanol, 2-(2-isopropylamino)propoxyethanol, tertiaryamylaminoethoxyethanol, or (1-methyl-2-ethylpropylamino)ethoxyethanol.

6. The process of claim 2 wherein the aqueous absorbent composition consists essentially of water and the 1-hydroxyethyl-4-pyridinlypiperazine compound.

* * * * *